United States Patent
Ojima et al.

(10) Patent No.: US 7,723,681 B2
(45) Date of Patent: May 25, 2010

(54) OBSERVATION METHOD WITH ELECTRON BEAM

(75) Inventors: Yuki Ojima, Mito (JP); Satoru Iwama, Hitachinaka (JP); Akira Ikegami, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 248 days.

(21) Appl. No.: 11/871,687

(22) Filed: Oct. 12, 2007

(65) Prior Publication Data

US 2008/0265160 A1  Oct. 30, 2008

(30) Foreign Application Priority Data

Oct. 13, 2006  (JP) .............. 2006-279920

(51) Int. Cl.
*G01N 23/04* (2006.01)

(52) U.S. Cl. .............. 250/311; 250/306; 250/307; 250/310; 250/396 ML; 250/492.2; 850/9

(58) Field of Classification Search .............. 250/306, 250/307, 310, 311, 396 ML, 492.1, 492.2, 250/492.3; 850/9
See application file for complete search history.

(56) References Cited

U.S. PATENT DOCUMENTS

| | | | |
|---|---|---|---|
| 5,412,209 A * | 5/1995 | Otaka et al. .............. 850/9 |
| 6,426,501 B1 * | 7/2002 | Nakagawa ................ 850/5 |
| 6,465,781 B1 * | 10/2002 | Nishimura et al. .......... 250/306 |
| 6,570,154 B1 | 5/2003 | Masnaghetti et al. |
| 6,635,873 B1 | 10/2003 | Todokoro et al. |
| 6,700,122 B2 * | 3/2004 | Matsui et al. .............. 250/310 |
| 6,946,656 B2 * | 9/2005 | Ezumi et al. ............... 850/11 |
| 7,187,345 B2 * | 3/2007 | Kobaru et al. ............. 345/10 |
| 2001/0035495 A1 * | 11/2001 | Nagai et al. ............... 250/311 |
| 2002/0134936 A1 * | 9/2002 | Matsui et al. .............. 250/310 |
| 2003/0057971 A1 * | 3/2003 | Nishiyama et al. .......... 324/751 |
| 2004/0211899 A1 * | 10/2004 | Ezumi et al. .............. 250/310 |
| 2005/0173657 A1 * | 8/2005 | Kadyshevitch et al. . 250/492.23 |
| 2005/0190310 A1 * | 9/2005 | Koyama et al. ............ 349/5 |
| 2006/0071167 A1 * | 4/2006 | Todokoro et al. .......... 250/310 |
| 2006/0134810 A1 * | 6/2006 | Bullock ................... 438/5 |

FOREIGN PATENT DOCUMENTS

| JP | 2000-200579 A | 7/2000 |
|---|---|---|
| JP | 2002-524827 A | 8/2002 |

* cited by examiner

*Primary Examiner*—David A Vanore
*Assistant Examiner*—Michael J Logie
(74) *Attorney, Agent, or Firm*—Crowell & Moring LLP

(57) ABSTRACT

For the purpose of repeatedly observing the bottom of a contact hole with a high aspect ratio, the potential of an electrostatic charge in each of a pattern to be observed and a vicinity of a range to be observed is stabilized by pre-charging a range on which to irradiate a beam of electrons while changing the range on a step-by-step basis.

9 Claims, 7 Drawing Sheets

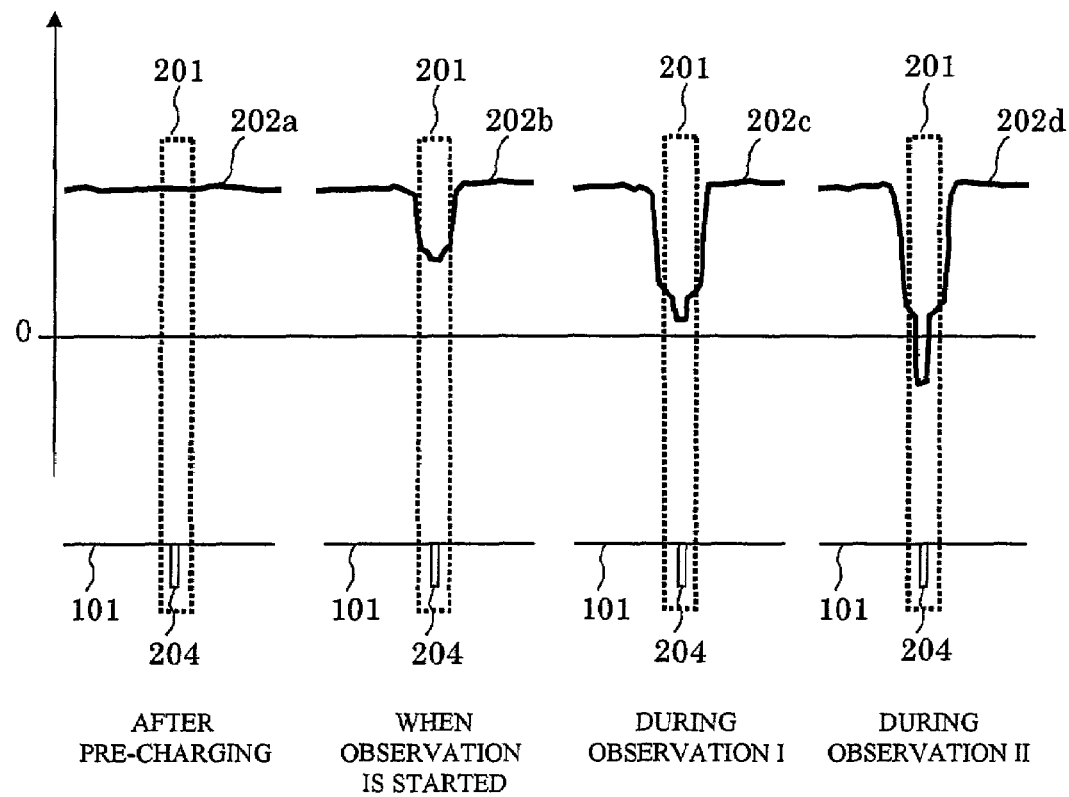

WHEN OBSERVATION IS STARTED

DURING OBSERVATION I

DURING OBSERVATION II

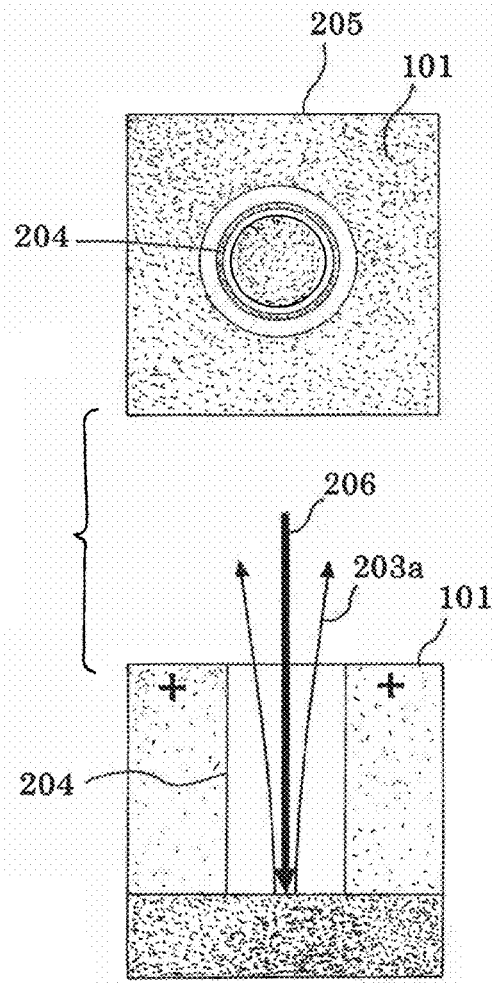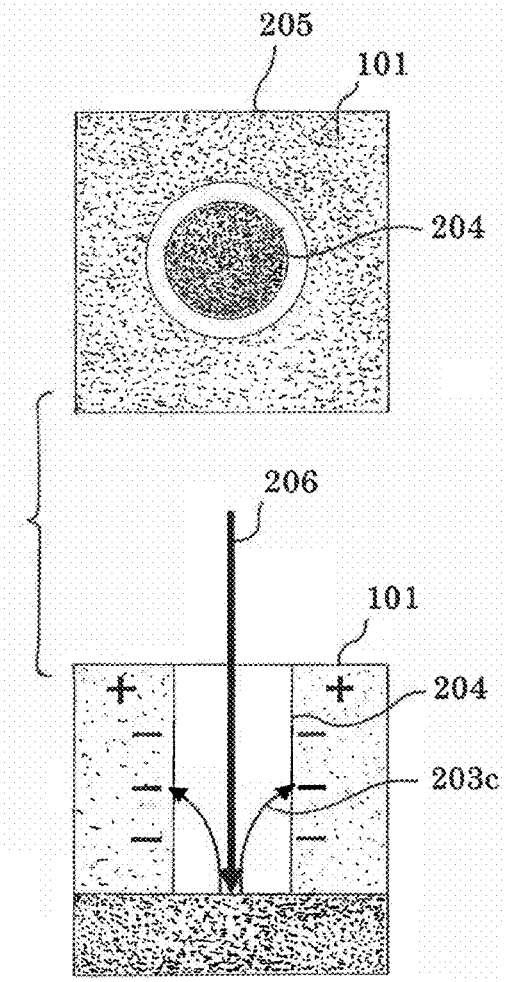
FIG. 4A — OBSERVATION RIGHT AFTER PRE-CHARGING
FIG. 4B — OBSERVATION WHILE PATTERN IS NEGATIVELY CHARGED

POTENTIAL OF ELECTROSTATIC CHARGE SEEN WHEN ONLY WIDER RANGE IS PRE-CHARGED

POTENTIAL OF ELECTROSTATIC CHARGE WHEN PRE-CHARGE ACCORDING TO PRESENT INVENTION IS CARRIED OUT

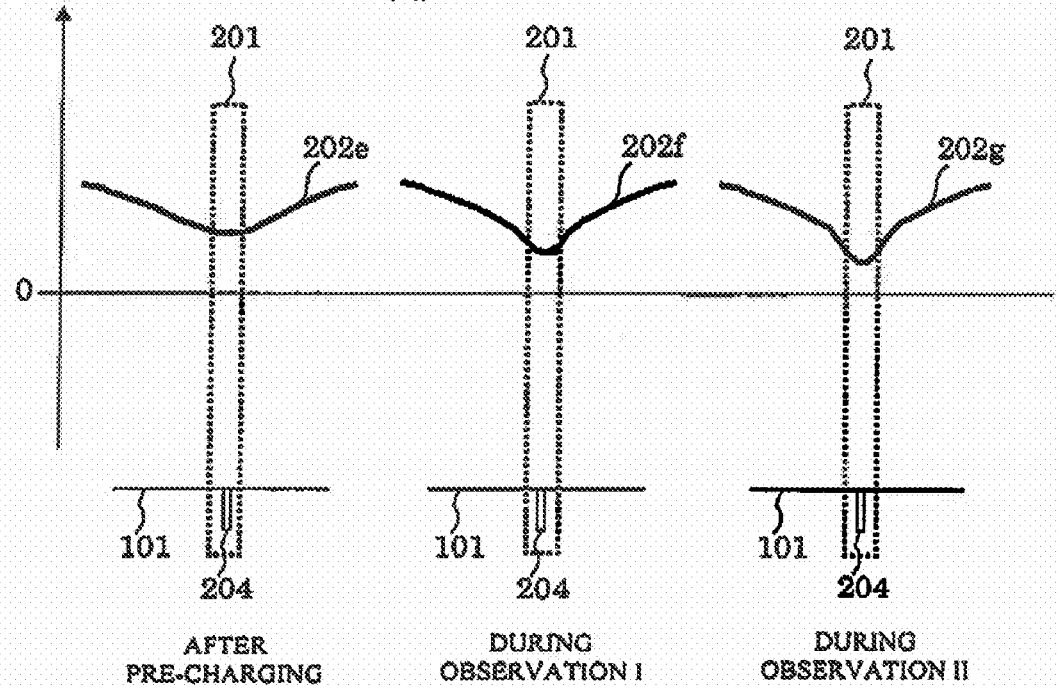
FIG. 6A AFTER PRE-CHARGING
FIG. 6B DURING OBSERVATION I
FIG. 6C DURING OBSERVATION II
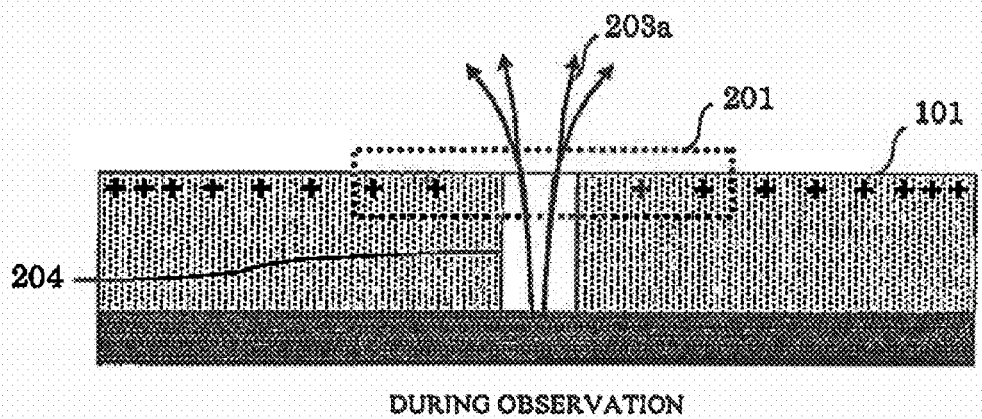
FIG. 7
DURING OBSERVATION

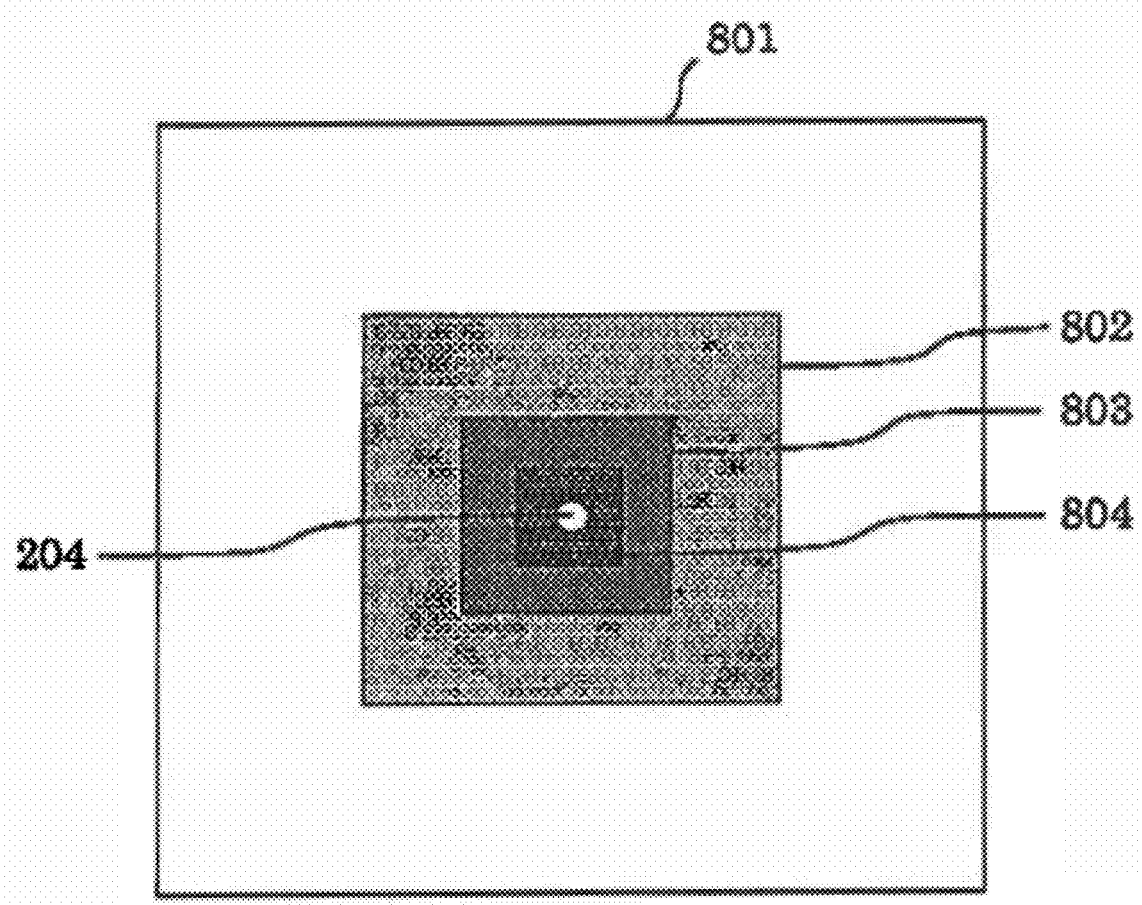

OBSERVATION METHOD WITH ELECTRON BEAM

CLAIM OF PRIORITY

The present application claims priority from Japanese application JP 2006-279920 filed on Oct. 13, 2006, the content of which is hereby incorporated by reference into this application.

BACKGROUND OF THE INVENTION

1. Field of the Invention

The present invention relates to a method of observing patterns using a beam of electrons, and particularly to a method of observing a contact hole using a beam of electrons.

2. Description of Related Art

Japanese Patent Application Laid-open Publication No. 2000-200579 describes a pre-charging method of observing a workpiece by use of an electron microscope by positively charging the surface of the workpiece. In the case of this method, a beam of electrons is irradiated on a wider range in the surface of the workpiece, or a beam of electrons is irradiated on the workpiece with a lower magnification, for the purpose of enhancing the pre-charging effect. Japanese Patent Translation Publication No. 2002-524827 describes a method of continuously observing a workpiece by an alternate series of observations and setups in a case where electrostatic charge in a spot to be observed is changed by a beam of electrons which is irradiated for observing the workpiece or acquiring an image of the workpiece. The setups are performed for controlling a condition in which the spot to be observed is electrostatically charged. To this end, the conditions under which a beam of electrons is irradiated on the spot to be observed are different from the observation conditions. According to this method of continuous observation, the setups and observations need to be carried out alternately and repeatedly. This is because each of the setups performed by irradiating a beam of electrons so that the electrostatic charge of the spot to be observed, which is generated while an image is being acquired, can be offset by the setups

SUMMARY OF THE INVENTION

In recent years, an inner diameter of each of contact holes becomes smaller in response to forming the patterns of each of semiconductor devices in a microscopic scale year after year. As a result, patterns each with a high aspect ratio (a ratio of the depth of a contact hole to the inner diameter thereof, a ratio obtained by dividing the depth by the inner diameter) need to be observed and measured more often than ever. In a conventional practice, the bottom of each contact hole with a higher aspect ratio is observed and measured after the surface of the workpiece is electrostatically charged positively by pre-charging. A conventional type of pre-charging method is feasible in a case where patterns each with a lower aspect ratio are observed, or in a case where patterns with a higher aspect ratio are observed only once. However, the conventional type of pre-charging method is apt to negatively charge contact holes as a result of lowering the electrical potential of the electrostatically-charged spot to be observed once the observation starts. The bottoms of the respective patterns each with a higher aspect ratio in particular are capable of being observed only once even if the surface of the workpiece is pre-charged. Otherwise, the bottoms of the respective patterns each with a higher aspect ratio look differently after the observation is repeatedly carried out. This makes it impossible to perform a stable observation or a stable dimensional measurement.

The pre-charging effect can be enhanced by changing the accelerating voltages or the amounts of probe current, too. However, if an observation and a measurement are carried out with a higher magnification by irradiating a beam of electrons on a narrower range in the surface of the workpiece, this reduces the pre-charging effect, and accordingly makes it difficult to observe the patterns repeatedly in some cases. As a result, a simple enhancement of the pre-charging effect alone cannot guarantee stable, repeated observation of the patterns because the pre-charging effect decreases depending on the conditions with which to observe the patterns. This makes it impossible to observe the patterns repeatedly or stably in some cases.

With this background taken into consideration, an object of the present invention is to provide a method which makes it possible to observe patterns each with a higher aspect ratio repeatedly and stably by pre-charging.

Decrease in the potential of the spot to be observed due to irradiation of a beam of electrons on a narrower range with a higher magnification is conceivable as a factor for making it difficult to repeatedly observe the patterns each with a higher aspect ratio. In addition that the irradiation of a beam of electrons on a narrower range with a higher magnification decreases the potential of the spot to be observed, this observation method further decreases the potential because secondary electrons are apt to be pushed back to the workpiece. Finally, the sidewall and bottom of each of the patterns become negatively charged. Once the spot to be observed becomes stable while negatively charged, secondary electrons generated from the bottom of each of the patterns are incapable of being detected even after the surface of the workpiece is pre-charged once more. This incapability makes it impossible to observe the patterns. For this reason, the potential of the spot to be observed needs to be prevented from decreasing for the purpose of enabling the bottoms of the respective patterns to be observed repeatedly. Particularly, the spot to be observed needs to be prevented from being negatively charged by forming an electric field where it is hard for secondary electrons generated from the bottom and sidewall of each of the patterns to return to the workpiece.

In the case of the present invention, the surface of the workpiece is pre-charged by changing the range on which a beam of electrons is irradiated on a step-by-step basis, and a moderate electric gradient is formed in a periphery of a range to be observed. This stabilizes the potential of the electrostatic charge in each of the patterns to be observed and a vicinity of the range to be observed. The formation of the moderate electric gradient in the periphery of the spot to be observed curbs a phenomenon in which secondary electrons generated while a beam electrons is being irradiated on the range are pushed back to the workpiece, and thus checks decrease in the potential in the spot to be observed. This makes it possible to detect secondary electrons efficiently, and makes the pre-charging effect last.

The method of observing a workpiece according to the present invention includes the steps of: irradiating a beam of electrons on a first region in the surface of a workpiece including a range to be observed; irradiating a beam of electrons on a range to be irradiated by narrowing down the range to be irradiated from the first range on a step-by-step basis; and observing the workpiece by irradiating a beam of electrons on the range to be observed. In addition, it is desirable that the method should further include the step of irradiating a beam of electrons on the range to be irradiated by enlarging the range to be irradiated on a step-by-step basis within an area narrower than the first region. While the range on which the beam of electrons is irradiated is changed on the step-by-step basis, it is desirable that the range should be changed with continuously irradiating the beam of electrons on the range to be irradiated instead of intermittently irradiating the beam of electrons thereon. In a case where the range on which the beam of electrons is irradiated is changed, the accelerating voltage, scan speed, and/or the amount of probe current may be changed simultaneously with the changing of the range on which the beam of electrons is irradiated.

The method of observing a workpiece according to the present invention further includes the steps of forming a moderate electric gradient around a contact hole formed in the workpiece on the surface of the workpiece in a periphery of the contact hole, and observing the contact hole by irradiating a beam of electrons on the contact hole, when observing the contact hole. The electric gradient is that which has a positive potential, and in which the potential in the vicinity of the contact hole is lower than the potential in positions father away from the contact hole The present invention makes it possible to stabilize the potential of the electrostatic charge in the patterns to be observed and the periphery of the range to be observed, and to accordingly observe the bottoms of the respective patterns stably and repeatedly.

BRIEF DESCRIPTION OF THE DRAWINGS

FIGS. 2A to 2D are diagrams showing a change in the potential of an electrostatic charge in a contact hole, which change is seen when the contact hole is observed by use of a conventional type of pre-charging method.

FIGS. 4A and 4B are diagrams showing how a pattern is electrostatically charged, and how an image looks.

FIGS. 6A to 6C are diagrams showing a change in the potential of an electrostatic charge, which is seen when a range to be observed is observed by use of the pre-charging method according to the present invention.

FIG. 7 is a diagram showing orbits of secondary electrons, and how a workpiece is electrostatically charged, which are seen when the range to be observed is observed by use of the pre-charging method according to the present invention.

FIG. 8 is a schematic diagram of a range on which a beam of electrons is irradiated by use of the pre-charging method according to the present invention.

DETAILED DESCRIPTION OF THE PREFERRED EMBODIMENT

Figure 3A:
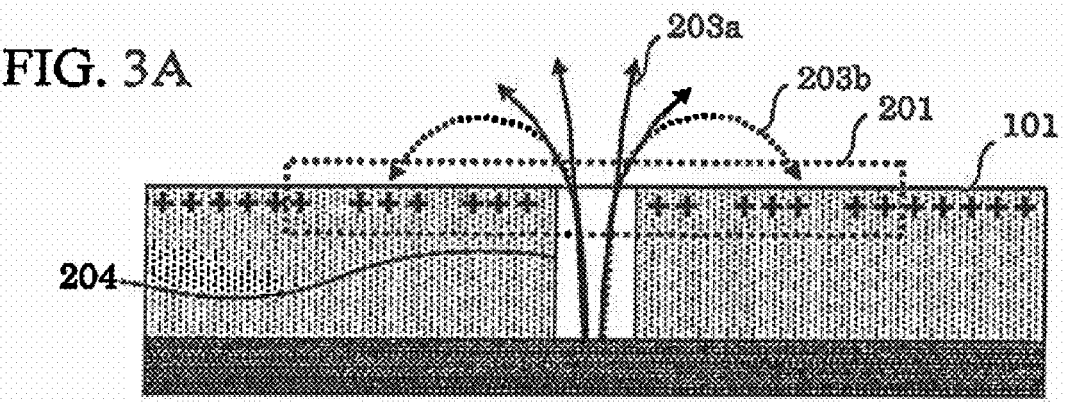
FIGS. 3A to 3C are diagrams showing orbits of secondary electrons, and how a workpiece is electrostatically charged, which are seen when the contact hole is observed by use of the conventional type of pre-charging method.
Figure 3B:
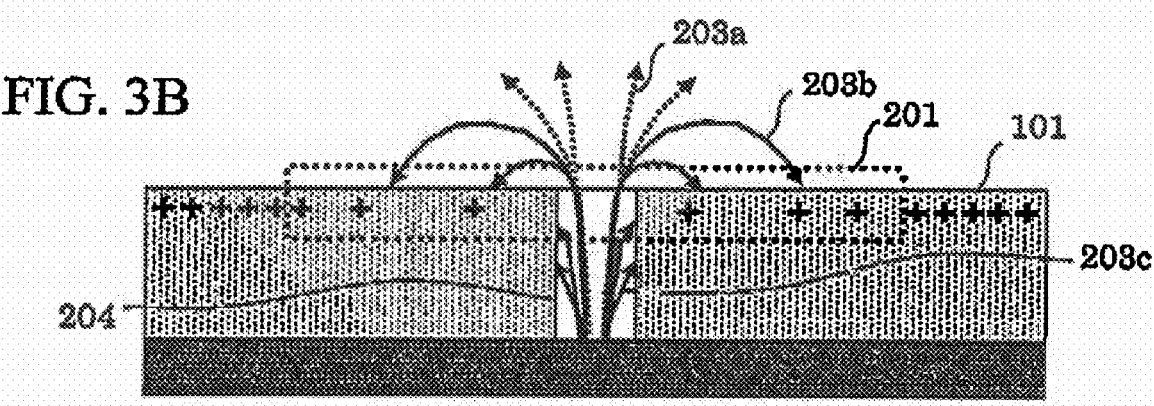
Figure 3C:
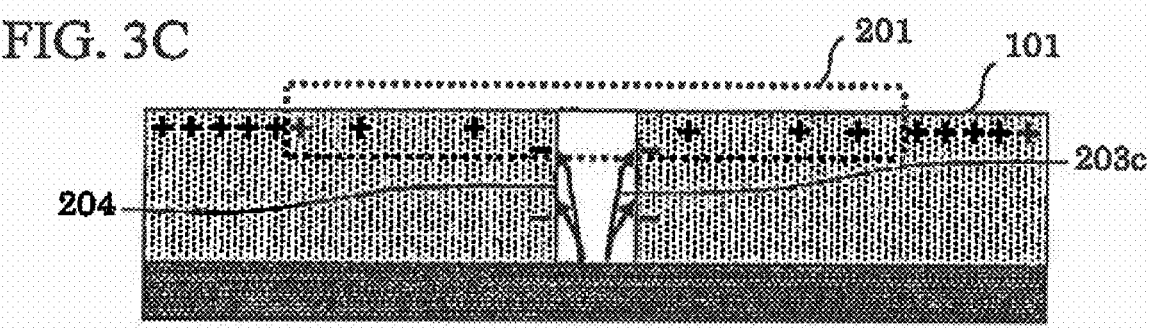

First of all, descriptions will be provided for what are problems with a conventional type of pre-charging method. FIGS. 2A to 2D are diagrams showing change in the potential of an electrostatic charge in a contact hole, which change is seen when the contact hole is observed with a higher magnification (when a narrower range is observed by irradiating a beam of electrons on the narrower range) by use of the conventional type of pre-charging method. FIGS. 3A to 3C are explanatory diagrams showing orbits of secondary electrons generated from the bottom of the contact hole.

As shown in FIG. 2A, the potential 202a of an electrostatic charge in the surface of a workpiece is overall high, right after a wider range in the surface of the workpiece is pre-charged. Once beam of electrons is irradiated on a narrower range in the surface of the workpiece in order that the workpiece can be observed with a higher magnification, the potential 202a of the electrostatic charge decreases in the observed range 201, as shown in FIG. 2B. FIG. 3A shows orbits of secondary electrons 203 which are seen when an observation is started. When observed immediately after pre-charged, secondary electrons 203a generated from the bottom of a contact hole 204 can be detected being accelerated due to the potential 202b of the electrostatic charge in the surface of the workpiece 101 because the potential 202b is high. At this time, however, orbits of secondary electrons 203b as parts of secondary electrons generated from the bottom of the contact hole are curved so that the secondary electron 203b returns to the workpiece, because the potential in a vicinity of the range to be observed is high as well.

If the beam of electrons continues being irradiated on the range to be observed for the observation, the potential decreases due to the irradiation of the beam of electrons. This reduces the force with which the secondary electrons are lifted up. As a result, orbits respectively of secondary electrons generated are apt to be curved more easily, and more secondary electrons return to the workpiece, as shown in FIG. 3B. The more secondary electrons return to the workpiece, the lower the potential 202c of the electrostatic charge in the range 201 to be observed becomes, as shown in FIG. 2C.

When the potential of the electrostatic charge decreases in the range 201 to be observed to a large extent, the contact hole 204 per se starts to be negatively charged gradually, as shown in FIG. 3B. Once the contact hole 204 per se is negatively charged completely, the contact hole 204 has an electrostatic potential 202d as shown in FIG. 2D. As a result, no secondary electrons 203c can escape from the contact hole 204, as shown in FIG. 3C. This makes it impossible to observe the bottom of the contact hole.

FIGS. 4A and 4B are schematic diagrams each showing an observation image 205 of the contact 204 and the cross-section thereof FIG. 4A shows a condition which is seen immediately after a pattern is pre-charged. FIG. 4B shows a condition which is seen when the pattern is negatively charged. While the bottom of the contact hole 204 in particular is being observed, if the sidewall of the contact hole 204 is negatively charged as shown in FIG. 4B, this negative charge makes it impossible to observe the secondary electrons 203c generated from the bottom of the contact hole 204. For this reason, when a contact hole is intended to be observed, the contact hole needs to be pre-charged lest the bottom and sidewall of the contact hole should be negatively charged. In particular, in a case where the workpiece is an easily charged material, such as an insulating material, negative charges which are injected into the sidewall of the pattern when the pattern is observed with a higher magnification remain in the sidewall. For this reason, the potential in the observed pattern remains low even though the surface of the workpiece is pre-charged once again. This makes it impossible to observe the pattern.

With these taken into consideration, in the case of the present invention, a wider range in the surface of a workpiece is positively charged once, as is the case with a conventional type of method. Thereafter, a moderate electric potential gradient is intentionally formed in a spot to be observed. This scheme reduces an influence of the potential which changes while the pattern is being observed with a higher magnification. The formation of the moderate electric potential gradient makes it possible to check orbits of the respective generated secondary electrons from being curved, and to check the secondary electrons from returning the workpiece. This makes it possible to prevent the potential in a vicinity of the spot to be observed from decreasing abruptly. Thereby, the contact hole per se will never be negatively charged. Accordingly, it is possible to observe the pattern by pre-charging the surface of the workpiece.

Figure 1:
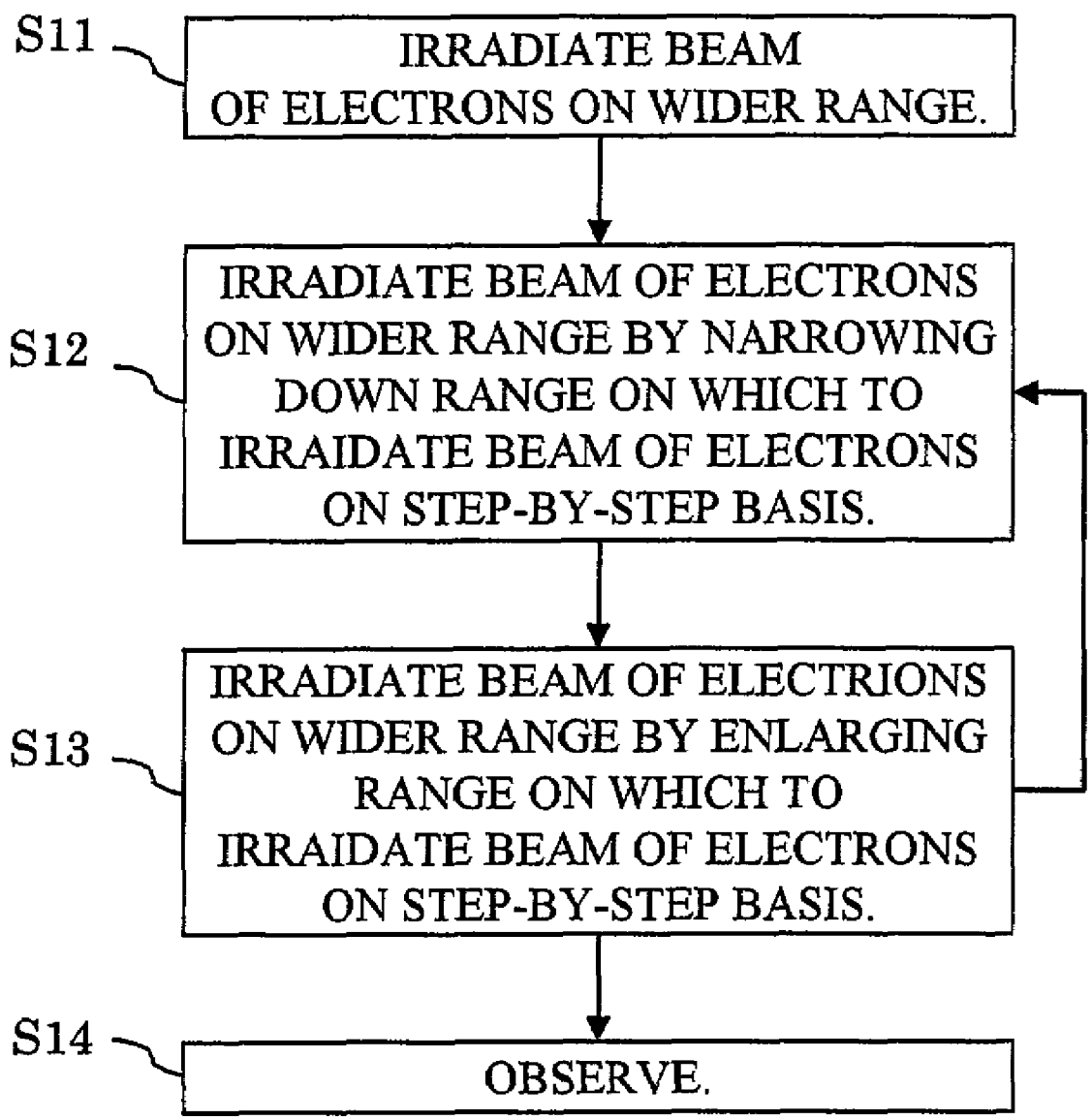
FIG. 1 is a flowchart of an observation which is performed by use of a pre-charging method according to the present invention.

FIG. 1 is a flowchart of the observation using the pre-charging method according to the present invention, in which the moderate electric potential gradient is formed in the vicinity of the spot to be observed. In addition, FIG. 8 shows a schematic diagram of a range to be pre-charge (a range on which a beam of electrons is irradiated).

In step S11, a beam of electrons is irradiated on a wider range in the surface 101 of the workpiece, and the spot to be observed is thus positively charged. In this respect, a larger area of positive electrostatic charge is formed in the surface 101 of the workpiece. First of all, as shown in FIG. 8, a beam of electrons is irradiated on a wider range 801, and the surface of the workpiece is thus pre-charged.

In other words, the surface of the workpiece is positively charged by pre-charging the wider range in the surface, or by pre-charging the surface with a lower magnification. In this respect, approximately 20 μm by approximately 20 μm to approximately 100 μm by approximately 100 μm can be listed as an example of the wider range. 1,000 times to 5,000 times can be listed as an example of the magnification. However, the wider range and the magnification are not necessarily limited to these numbers. If the wider range is pre-charged by irradiating the beam of electrons on the wider range in this manner, this makes it possible to make the positive electrostatic charge larger, and to accordingly make the potential of the electrostatic charge larger. The wider range the beam of electrons is irradiated on, the larger the maximum amount of the electrostatic charge becomes. In particular, in a case where the surface of the workpiece is positively pre-charged, the pre-charging effect is larger when the beam of electrons is irradiated on the surface of the workpiece under a condition that excited secondary electrons are larger in number than electrons irradiated on the surface of the workpiece. The surface of the workpiece is easier to be positively charged when the amount of probe current for each scan is smaller. For this reason, the larger the number of times that a beam of electrons is scanned in a wider range with a lower probe current at a higher speed repeatedly, the more efficiently the surface of the workpiece can have a potential of the positive electrostatic charge.

In addition, the beam of electrons needs to be irradiated on the surface of the workpiece repeatedly in order for the potential of the electrostatic charge to be saturated. In this context, the irradiation time also needed to be increased in order to enhance the effect of pre-charging the surface of the workpiece to the positive electrostatic charge. Moreover, as the amount of the beam of electrons irradiating on the surface of the workpiece is increased, the potential of the electrostatic charge becomes saturated more quickly. This slightly reduces the maximum value of the potential of the electrostatic charge. However, the increasing of the amount of the probe current makes it possible to pre-charge the surface of the workpiece at a higher speed.

The effect of pre-charging the surface of the workpiece positively is that the pre-charging makes it easier to observe the bottom of the pattern, because the potential difference between the surface of the workpiece and the bottom of the pattern lifts up secondary electrons generated from the bottom of the pattern. However, the merely increasing of the potential of the electrostatic charge in the surface of the workpiece cannot enhance the number of repeated observations to a large extent.

With this taken into consideration, in the case of the present invention, the beam of electrons is irradiated on the surface of the workpiece by narrowing the range on which to irradiate the beam of electrons for the purpose of forming the moderate electric potential gradient in the spot to be observed, in step S12. At this time, the range on which to irradiate the beam of electrons is gradually narrowed down to the range to be observed. Nevertheless, the beam of electrons need not be preliminarily irradiated on the surface of the workpiece with a magnification raised to the magnification employed for the observation to be carried out. In addition, the range on which to irradiate the beam of electrons is changed on a step-by-step basis, or continuously. If the beam of electrons is irradiated thereon without interruption, the potential of the electrostatic charge changes smoothly. For this reason, the beam of electrons had better be irradiated on the range to irradiate the beam of electrons without interruption while the range is being changed.

Step S12 will be illustrated by use of FIG. 8 showing pre-charged ranges. The beam of electrons is irradiated on the range on which to irradiate the beam of electrons by narrowing down the area from the range 801 to a range 802, a range 803 and a range 804 sequentially.

While the range on which to irradiate the beam of electrons is larger, the potential of the electrostatic charge is larger. As the range on which to irradiate the beam of electrons is narrowed down, the scanning speed becomes lower, and an amount of the beam of electrons irradiated for a unit area becomes larger. As a result, the potential of the electrostatic charge becomes smaller. This makes it possible to make the potential of the electrostatic charge in the spot to be observed lower than the potential of the electrostatic charge in the periphery of the spot to be observed by narrowing down the range on which to irradiate the beam of electrons on a step-by-step basis or continuously. In addition, the condition in which the surface of the workpiece is electrostatically charged and the potential of the surface thereof are capable of being controlled by changing the amount of the beam of electrons irradiated on the surface thereof depending on the range on which to irradiate the beam of electrons as well, as a method other than the method in which the scanning speed is changed depending on the range on which to irradiate the beam of electrons. These methods may be used in combination.

In step S13, the range on which to irradiate the beam of electrons is enlarged on a step-by-step basis or continuously once the range on which to irradiate the beam of electrons is smaller. FIG. 8 illustrates that the range on which to irradiate the beam of electrons is enlarged from the range 804, the range 803, the range 802 to the range 801 sequentially. At this time, the range on which to irradiate the beam of electrons need not be larger than the range on which the beam of electrons has been irradiated in step S11, and may be smaller than the range 801 on which the beam of electrons has been irradiated in step S11. It should be noted that the range on which to irradiate the beam of electrons had better be changed by irradiating the beam of electrons thereon without interruption. It is desirable that the beam of electrons should be irradiated thereon without interruption while the flow proceeds from step S12 to step S13, and that this should be the case with the flow which proceeds from step S13 to step S12.

If steps 12 and 13 are further carried out after step S13 is carried out, this makes it possible to form a stable and moderate electric potential gradient, and to accordingly form a stable potential of the positive electrostatic charge. In step S13, if, for the last time, the surface of the workpiece is pre-charged by irradiating the beam of electrons on the wider range 801 in the surface thereof after repeating carrying out steps S12 and S13 before the observation, this pre-charging makes it possible to enlarge the positive electrostatic charge, and to accordingly observe the pattern stably in step S14.

Figure 5A:
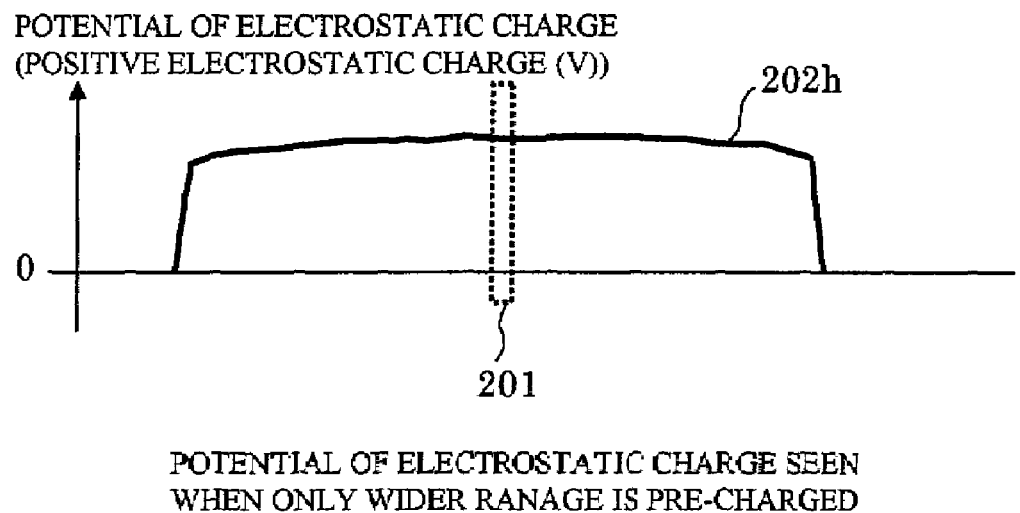
FIGS. 5A and 5B are diagrams showing the difference between the conventional type of pre-charging method and the pre-charging method according to the present invention in the potential of the electrostatic charge.
Figure 5B:
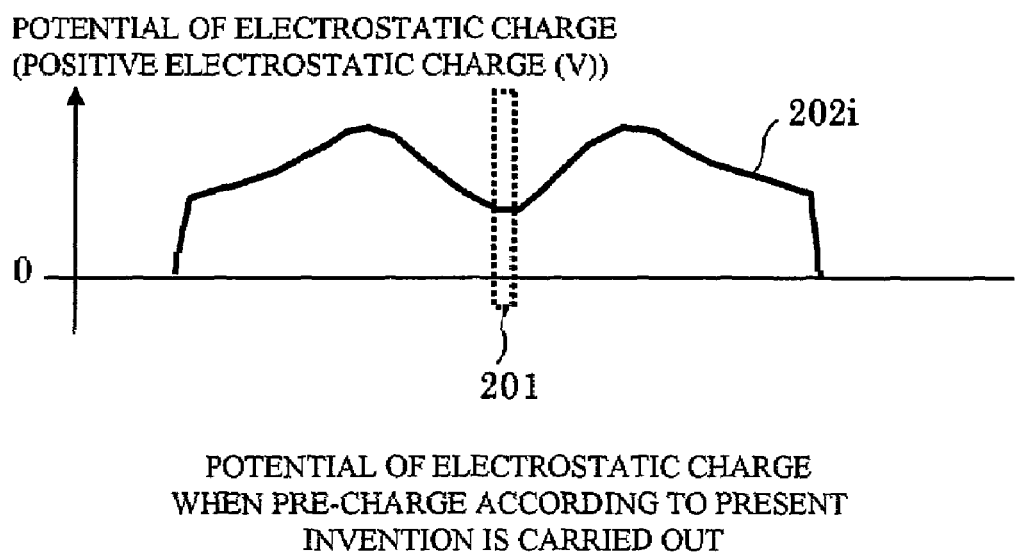

FIGS. 5A and 5B are schematic diagrams showing the difference in the potential of the electrostatic charge between a conventional type of pre-charging method (one-time pre-charging in a wider range) and the pre-charging method according to the present invention. In the case of the conventional method in which a wider range is pre-charged once, as shown in FIG. 5A, a potential 202h of the electrostatic charge in the pre-charged range is evenly high, and an abrupt electric potential gradient exists only in each boundary between ranges on which to irradiate the beam of electrons. For this reason, the potential 202h of the electrostatic charge in the range 201 to be observed is equal to the potential 202h of the electrostatic charge in the periphery of the range 201 to be observed. On the other hand, in the case of the pre-charging method according to the present invention, the potential of the electrostatic charge of each of the range 201 to be observed and the vicinity of the range 201 is lower than the potential of the electrostatic charge of their surroundings.

FIGS. 6A to 6C are diagrams showing change in the potential of the electrostatic charge, which change is seen when an observation is carried out with the moderate electric potential gradient formed in the periphery. In addition, FIG. 7 is a diagram showing orbits of secondary electrons and how the workpiece is electrostatically charged, which are seen when the observation is carried out with the moderate electric potential gradient present in the periphery of the region to be observed.

As shown in FIG. 6A, the potential 202e of the electrostatic charge in the spot to be observed is beforehand lower than the potential 202e of the electrostatic charge in the periphery of the spot to be observed. Moreover, because the potential 202e of the electrostatic charge in each of the spot to be observed and the vicinity of the spot is beforehand lower as shown in FIG. 6A, the orbits of the respective secondary electrons 203a are curved less, and this makes it possible to check the secondary electrons from returning to the surface of the workpiece, even though the potential of the electrostatic charge slightly decreases while the observation is being carried out with the higher magnification as shown in FIG. 6B. For this reason, the potential of the electrostatic charge does not decrease abruptly in the range 201 to be observed. This makes it possible to minimize the decrease in the potential of the electrostatic charge in the range 201 to be observed. Accordingly, it is possible to keep the potential 202g of the electrostatic charge in the contact hole 204 positive as shown in FIG. 6C, and to observe the contact hole stably. Furthermore, in the case of this method, it is possible to observe the bottom of the contact hole 204 repeatedly, because the potential of the electrostatic charge in the contact hole 204 is positive.

If the irradiation of the beam of electrons on the narrower range with the higher magnification is interrupted while the irradiation is being carried out, no electrons are injected into the workpiece locally. This changes the condition in which the range 201 to be observed is electrostatically charged. In a case where the irradiation of the beam of electrons on the narrower range is going to be interrupted, the irradiation can be interrupted after the beam of electrons is irradiated on a range wider than the range to be observed. If the irradiation is interrupted in this manner, this makes it possible to check the potential of the electrostatic charge from decreasing, and to accordingly observe the bottom of the contact hole repeatedly and stably.

In the case of the foregoing embodiment, the surface of the workpiece is positively charged and thus pre-charged by irradiating the beam of electrons on the surface of the workpiece. It should be noted, however, that a moderate electric potential gradient may be formed by electrostatically charging a vicinity of the spot to be observed by use of a method other than the method in which a beam of electrons is irradiated thereon. Thereby, if the potential in each of the spot to be observed and the vicinity of the spot to be observed is beforehand set lower than the potential of their periphery, this makes it possible to reduce the phenomenon in which orbits respectively of secondary electrons are curved toward the range to be observed and the pattern thereof so that the secondary electrons are pushed back to the range and the pattern. As a result, it is possible to check the pattern and the spot to be observed from being negatively charged, and to accordingly check the potential in each of the pattern and the spot to be observed from decreasing while the observation is being carried out with the higher magnification, and after the observation is carried out. Employment of the present invention makes it possible to observe the bottom of the pattern stably, and to accordingly observe the bottom of the pattern repeatedly and stably.

In a case where the bottom of a microscopic pattern in a semiconductor device and the like is intended to be observed and measured, employment of the present invention makes it possible to observe and measure the bottom of the pattern, and additionally to observe and measure the bottom thereof repeatedly.

What is claimed is:

1. A method of observing a workpiece, comprising:
   irradiating a beam of electrons on a first region, including a a hole pattern, in a surface of the workpiece such that the first region is electrostatically charged positively;
   irradiating the beam of electrons by making a range on which to irradiate the beam of electrons narrower than the first region on a step-by-step basis such a potential of the electrostatic charge becomes lower in positions closer to the hole pattern; and
   observing a range to be observed including the hole pattern by irradiating the beam of electrons on the range to be observed.

2. The method of observing a workpiece as recited in claim 1, further comprising the step of irradiating the beam of electrons by making the range on which to irradiate the beam of electrons wider within a range narrower than the first region on a step-by-step basis.

3. The method of observing a workpiece as recited in claim 1, wherein the range on which to irradiate the beam of electrons is changed while the beam of electrons is being continuously irradiated on the range on which to irradiate the beam of electrons.

4. The method of observing a workpiece as recited in claim 1, wherein a bottom of a contact hole formed in the workpiece is observed.

5. The method of observing a workpiece as recited in claim 1, wherein the observation is carried out by irradiating the beam of electrons in a range wider than the range to be observed before the observation is carried out.

6. The method of observing a workpiece as recited in claim 1, wherein, when the range on which to irradiate the beam of electrons is changed, conditions for irradiating the beam of electrons on the range are simultaneously changed.

7. The method of observing a workpiece as recited in claim 6, wherein the conditions for irradiating the beam of electrons on the range are on at least one of an accelerating voltage, a scanning speed and an amount of probe current.

8. A method of observing a workpiece for observing a contact hole formed in the workpiece, comprising:

forming a moderate electric potential gradient in a vicinity of the contact hole in the workpiece; and observing the contact hole by irradiating a beam of electrons on the contact hole by using a range on which to irradiate the beam narrower than a first region in a step-by-step basis such that a potential is lower closer to a contact hole.

9. The method of observing a workpiece as recited in claim 8, wherein the electric potential gradient is formed in a way that the potential in the vicinity of the contact hole is lower than that in an outer periphery of the vicinity of the contact hole.

* * * * *